United States Patent
Astier et al.

(10) Patent No.: US 9,057,693 B2
(45) Date of Patent: Jun. 16, 2015

(54) SILICON OXIDE NANOPORE WETTING AND STABILIZATION BY MOLECULAR COATING

(71) Applicants: International Business Machines Corporation, Armonk, NY (US); 454 Life Sciences Corporation, Brandford, CT (US)

(72) Inventors: Yann Astier, White Plains, NY (US); Venkat K. Balagurusamy, Suffern, NY (US); Steven Lefkowitz, Branford, CT (US)

(73) Assignees: International Business Machines Corporation, Armonk, NY (US); 454 Life Sciences Corporation, Brandford, CT (US)

( * ) Notice: Subject to any disclaimer, the term of this patent is extended or adjusted under 35 U.S.C. 154(b) by 53 days.

(21) Appl. No.: 13/872,410

(22) Filed: Apr. 29, 2013

(65) Prior Publication Data

US 2014/0318966 A1   Oct. 30, 2014

(51) Int. Cl.
| | |
|---|---|
| *G01N 27/00* | (2006.01) |
| *G01N 27/447* | (2006.01)\ |
| *G01N 33/48* | (2006.01) |
| *C12Q 1/68* | (2006.01) |
| *G01N 21/75* | (2006.01) |
| *B01L 3/00* | (2006.01) |
| *G01N 33/543* | (2006.01) |
| *G01N 33/487* | (2006.01) |
| *G01N 27/414* | (2006.01) |
| *G01N 27/327* | (2006.01) |

(52) U.S. Cl.
CPC .......... *G01N 27/4473* (2013.01); *C12Q 1/6806* (2013.01); *G01N 2021/757* (2013.01); *B01L3/502753* (2013.01); *C12Q 1/6869* (2013.01); *G01N 33/54373* (2013.01); *G01N 33/48721* (2013.01); *C12Q 1/6841* (2013.01); *C12Q 2521/101* (2013.01); *B01L 3/5023* (2013.01); *B01L 2400/086* (2013.01); *B01L 2300/0816* (2013.01); *G01N 27/414* (2013.01); *G01N 33/54393* (2013.01); *G01N 27/3271* (2013.01); *G01N 33/5438* (2013.01); *G01N 33/48* (2013.01)

(58) Field of Classification Search
CPC ............... C12Q 1/6869; C12Q 1/6874; C12Q 2565/518; C12Q 1/68; C12Q 1/6816; C12Q 1/683; C12Q 1/6841; C12Q 2561/113; C12Q 1/6806; C12Q 2521/101; G01N 27/4146; G01N 27/3275; G01N 33/48721; G01N 33/54393; G01N 2021/757; G01N 27/3271; G01N 33/5438; G01N 27/414; G01N 33/54373; B82Y 15/00; B82Y 30/00; B82Y 5/00; B82Y 99/00; B01L 2300/0636; B01L 2300/0816; B01L 2400/086; B01L 3/5023; B01L 3/502753
USPC ......... 422/52, 73, 82.01, 82.05, 82.08, 82.09, 422/82.11, 99, 102, 400, 401, 420, 421, 422/422, 423, 424, 425, 426, 427, 428, 429, 422/68.1, 501, 502, 503, 504; 436/164, 436/177, 43, 63; 435/29, 4, 6, 7.1
See application file for complete search history.

(56) References Cited

U.S. PATENT DOCUMENTS

| | | |
|---|---|---|
| 6,677,251 B1 | 1/2004 | Lu et al. |
| 8,137,569 B2 | 3/2012 | Harnack et al. |
| 8,325,339 B2 | 12/2012 | Ebstein |
| 2007/0020146 A1 | 1/2007 | Young et al. |
| 2009/0136958 A1 | 5/2009 | Gershow et al. |
| 2011/0053284 A1 | 3/2011 | Meller et al. |
| 2011/0174629 A1 | 7/2011 | Bouchet et al. |

FOREIGN PATENT DOCUMENTS

| | | | |
|---|---|---|---|
| WO | WO 2012027561 A1 | * | 3/2012 |
| WO | WO 2012142174 A1 | * | 10/2012 |

OTHER PUBLICATIONS

Chang et al.,"DNA-Mediated Fluctuations in Ionic Current through Silicon Oxide Nanopore Channels" Nano Letters, Jul. 7, 2004, vol. 4 (8), pp. 1551-1556.*

Unpublished Application by Balagurusamy, Venkat K., "Nonopore Device Wetting" U.S. Appl. No. 13/524,069, filed Jun. 15, 2012.

Danelon et al., "Fabrication and Functionalization of Nanochannels by Electron-Beam-Induced Silicon Oxide Deposition", Langmuir 2006, 22. pp. 10711 through 10715.

Li et al., "DNA molecules and configurations in a solid-state nanopore microscope", Nature materials, vol. 2, No. 9, 2003, pp. 611-615.

Lu et al., "Eletrowetting Effect in a Nanoporous Silica," Langmuir, vol. 25, No. 16, 2009, pp. 9463-9466.

Nilsson et al., "Localized functionalization of single nanopores," Lawrence Livermore National Laboratory, Report UCRL-JRNL-215327, Sep. 13, 2005, 15 pages.

Storm et al., "Translocation of double-strand DNA through a silicon oxide nanopore", Physical Review E71, 051903 (2005), pp. 051903-1 through 51903-10.

White et al., "Single ion-channel recordings using glass nanopore membranes," Journal of the American Chemical Society, vol. 129, No. 38, 2007, pp. 11766-11775.

\* cited by examiner

*Primary Examiner* — Dennis M White (74) *Attorney, Agent, or Firm* — Cantor Colburn LLP; Vazken Alexanian (57) ABSTRACT

A nanopore device includes a multi-layer structure comprising a surface defining an aperture extending through the multi-layer structure, wherein at least the surface comprising a minimal diameter comprises a monosilane functionalized silicon dioxide having a silicon-oxygen-silicon bond, the monosilane functionalized silicon dioxide having the following structure:

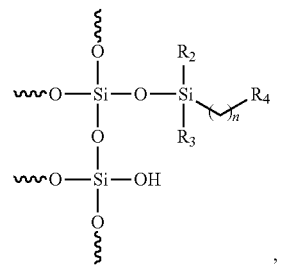

wherein n is an integer from 1 to 12; $R_2$ and $R_3$ are each independently a methyl group, an ethyl group, a propyl group, an isopropyl group, a butyl group, or a tert-butyl group; and $R_4$ is a chloride, a carboxylic acid group, an amine group, an amide group, a thiol group, an alcohol group, an acyl chloride group, an acyl bromide group, an acyl iodide group, an alkene group, an alkyne group, or a polyether group. Also disclosed are methods for making, wetting, and operating the nanopore device.

19 Claims, 7 Drawing Sheets

SILICON OXIDE NANOPORE WETTING AND STABILIZATION BY MOLECULAR COATING

BACKGROUND

The present disclosure generally relates to nanopore devices, and more specifically, to silicon dioxide nanopore wetting and stabilization by molecular coating.

Nanopore devices can be used for DNA sequencing and to study DNA-protein interactions. These devices can include a multi-layer structure having at least a single aperture, or "nanopore," and a pair of cavities disposed on opposing sides of the nanopore. The cavities are operative to receive fluids which can include molecules, for example DNA, RNA, proteins, or cells. The dimensions and compositions of nanopore devices can be tailored to the desired application.

In operation, an electrical potential difference is generated across the multi-layer structure having the nanopore by applying a voltage. Subsequently, the ionic current passing through the nanopore is measured. When the nanopore is of molecular dimensions, passage of molecules, e.g., DNA, induce interruptions in the open current level. A detected interruption, or ionic current drop, indicates passage of a single molecule through the nanopore, which can also be referred to as a translocation event.

SUMMARY

In one embodiment of the present disclosure, a nanopore device comprises a multi-layer structure comprising a surface defining an aperture extending through the multi-layer structure. At least the surface comprising a minimal diameter comprises a monosilane functionalized silicon dioxide having a silicon-oxygen-silicon bond, and the monosilane functionalized silicon dioxide has the following structure:

wherein n is an integer from 1 to 12; $R_2$ and $R_3$ are each independently a methyl group, an ethyl group, a propyl group, an isopropyl group, a butyl group, or a tert-butyl group; and $R_4$ is a chloride, a carboxylic acid group, an amine group, an amide group, a thiol group, an alcohol group, an acyl chloride group, an acyl bromide group, an acyl iodide group, an alkene group, an alkyne group, or a polyether group.

In another embodiment, a method for making a nanopore device comprises fabricating an aperture in a multi-layer structure comprising silicon dioxide; and substantially functionalizing an exposed surface of the silicon dioxide with a monosilane to form a silicon-oxygen-silicon bond and a monolayer on the surface of the silicon dioxide. The monosilane functionalized silicon dioxide has the following structure:

wherein n is an integer from 1 to 12; $R_2$ and $R_3$ are each independently a methyl group, an ethyl group, a propyl group, an isopropyl group, a butyl group, or a tert-butyl group; and $R_4$ is a chloride, a carboxylic acid group, an amine group, an amide group, a thiol group, an alcohol group, an acyl chloride group, an acyl bromide group, an acyl iodide group, an alkene group, an alkyne group, or a polyether group.

Yet, in another embodiment, a method for operating a nanopore device comprises filling a first cavity and a second cavity of the nanopore device with a first buffered salt solution, wherein the nanopore device comprises a multi-layer structure comprising a surface defining an aperture extending through the multi-layer structure. At least the surface comprising a minimal diameter of the aperture comprises a monosilane functionalized silicon dioxide having a silicon-oxygen-silicon bond, and the monosilane functionalized silicon dioxide has the following structure:

wherein n is an integer from 1 to 12; $R_2$ and $R_3$ are each independently a methyl group, an ethyl group, a propyl group, an isopropyl group, a butyl group, or a tert-butyl group; and $R_4$ is a chloride, a carboxylic acid group, an amine group, an amide group, a thiol group, an alcohol group, an acyl chloride group, an acyl bromide group, an acyl iodide group, an alkene group, an alkyne group, or a polyether group. The method further comprises introducing an analyte into the first cavity, applying a voltage in the nanopore device, and measuring a current in the nanopore device. The current has a current path defined by the first cavity, the second cavity, and the aperture, wherein the aperture is in fluid communication with the first cavity and the second cavity. Further, the current is affected by the analyte passing proximate to or through the aperture.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

As used herein, the term "monosilane" refers to a molecule having the following structure:

wherein n is an integer from 1 to 12; $R_1$ is a methyl group, an ethyl group, a propyl group, a butyl group, a pentyl group, or a hexyl group; $R_2$ and $R_3$ are each independently a methyl group, an ethyl group, a propyl group, an isopropyl group, a butyl group, or a tert-butyl group; and $R_4$ is a chloride, a carboxylic acid group, an amine group, an amide group, a thiol group, an alcohol group, an acyl chloride group, an acyl bromide group, an acyl iodide group, an alkene group, an alkyne group, or a polyether group. The amine group can be a primary amine, a secondary amine, or a tertiary amine. An exemplary monosilane is 3-aminopropyl-dimethyl-ethoxysilane (APDMES). Other non-limiting examples of mono silanes include any alkoxysilanes, including methoxysilanes and ethoxysilanes.

As used herein, the term "substantially stable" current refers to current fluctuations being less than about 5% of the maximum measured current. For example, if the measured current is 100 nano amperes (nA) at 1 volt (V), the maximum expected fluctuation will only be 5 nA. Accordingly, the term "substantially unstable" current refers to the nanopore current showing fluctuations greater than about 5% of the maximum current in a short time scale, for example, about 0.1 seconds.

As used herein, the term "multilayer structure" refers to a substrate such as silicon and at least one layer of silicon oxide. The multilayer structure may include multiple silicon dioxide layers and may also include one or more non-silicon dioxide layers as may be desired for different devices.

Figure 1:
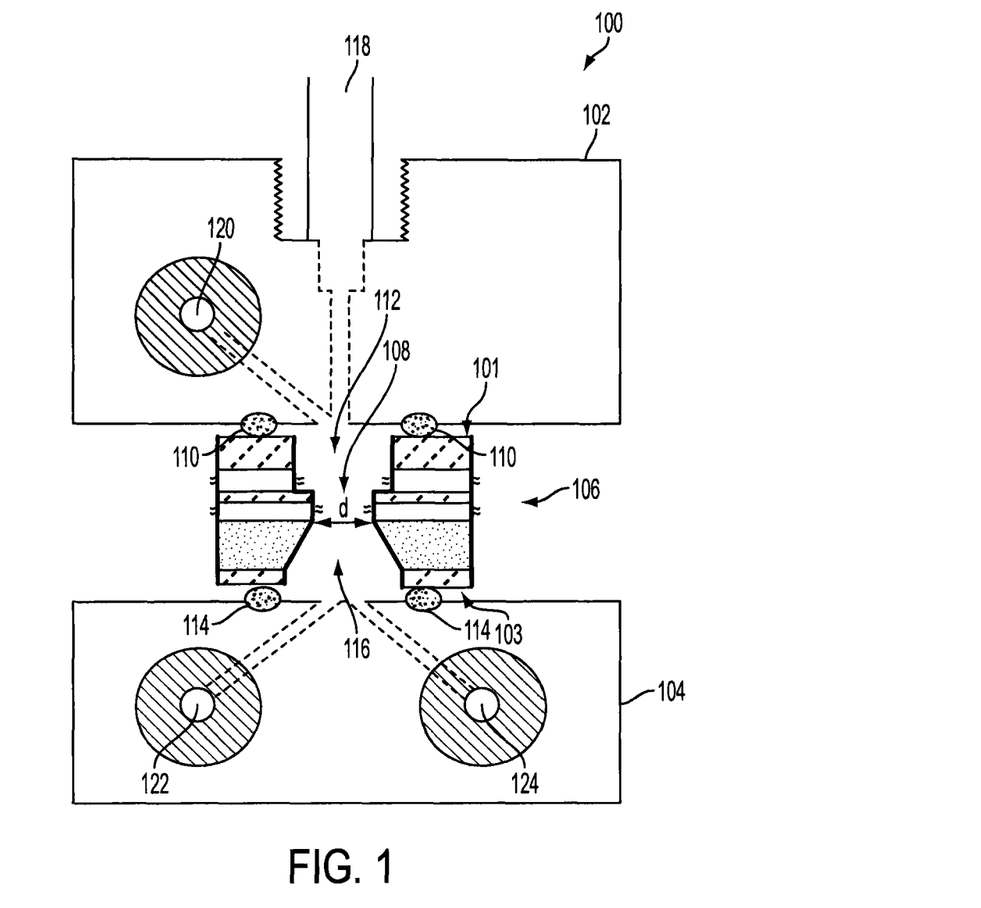
FIG. 1 illustrates a partially cut-away front view of an exemplary embodiment of a nanopore device.
Figure 2:
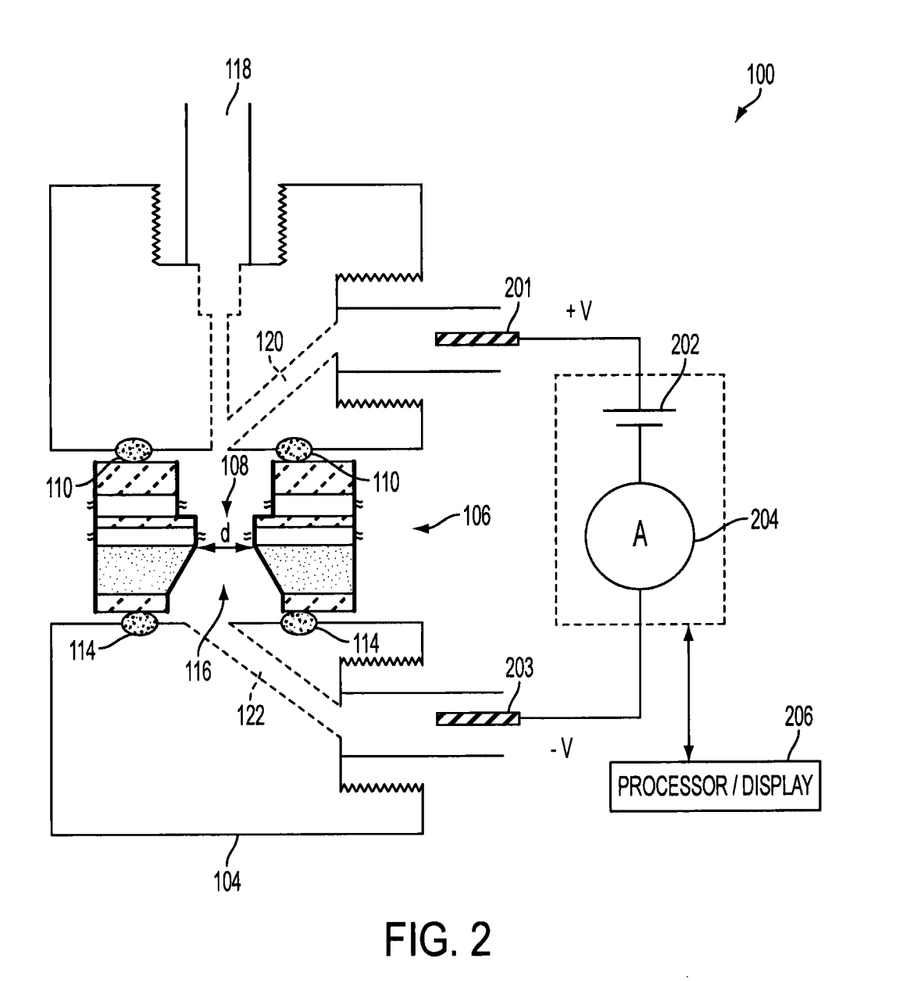
FIG. 2 illustrates a partially cut-away side view of the exemplary embodiment of a nanopore device of FIG. 1.

FIG. 1 and FIG. 2 illustrate a partially cut-away front and side view, respectively, of an exemplary embodiment of a nanopore device 100. Referring to FIG. 1, the nanopore device 100 defines a fluidic cell having a first cell portion 102 and a second cell portion 104. A DNA transistor device, or nanopore chip, 106, is disposed between the first cell portion 102 and the second cell portion 104. The nanopore chip 106 includes a multi-layer structure having a first surface 101 and an opposing second surface 103. The multi-layer structure comprises a surface defining an aperture (i.e., a nanopore) 108 extending through the multi-layer structure from the first surface 101 to the second surface 103. At least the surface comprising a minimal diameter comprises a monosilane functionalized silicon dioxide having a silicon-oxygen-silicon bond.

The diameter of the aperture 108 generally varies but narrows down to a dimension desirable for the intended application. The particular size is not intended to be limited. The aperture 108 diameter is defined as the narrowest diameter through the multi-layer structure, not including the monosilane functionalized portion on the surface. In some embodiments, the narrowest or minimal diameter, i.e., nanopore diameter, is from about 5 nm to 60 nm; in other embodiments, the nanopore diameter is from about 20 nm to 100 nm; and in still other embodiments, the nanopore diameter is from about 100 nm to 500 nm.

A first seal portion 110 is sealingly engaged between the first cell portion 102 and the first surface 101 of the nanopore chip 106. The nanopore chip 106, the first seal portion 110 and the first cell portion 102 define a first cavity 112 of the aperture 108. A second seal portion 114 is sealingly engaged between the second surface 103 of the nanopore chip 106 and the second cell portion 104. The nanopore chip 106, the second seal portion 114, and the second cell portion 104 define a second cavity 116 of the aperture 108. The aperture 108 further comprises first and second cavities being fluidically connected via the aperture 108. The first seal portions 110 and 114 can be o-ring gaskets made of, for example, silicon. The first cell portion 102 defines a first port 118 and a second port 120 that are in fluid communication with the first cavity 112. The second cell portion 104 defines a third port 122 and a fourth port 124 that are in fluid communication with the second cavity 116.

Referring to FIG. 2, a voltage source 202 is shown arranged with electrodes 201 and 203 disposed in the second port 120 and the third port 122. A current sensing device 204, for example, an Axopatch 200B current amplifier available from Molecular Devices, Sunnyvale, Calif., is operative to detect changes in current between the electrodes 201 and 203. The current sensing device 204 can be controlled by a personal computer through operative software. The current has a current path defined by the first cavity 112, the second cavity 116, and the aperture 108. The nanopore device 100 is but an exemplary embodiment. Other embodiments of the nanopore device 100 may be used.

Figure 3:
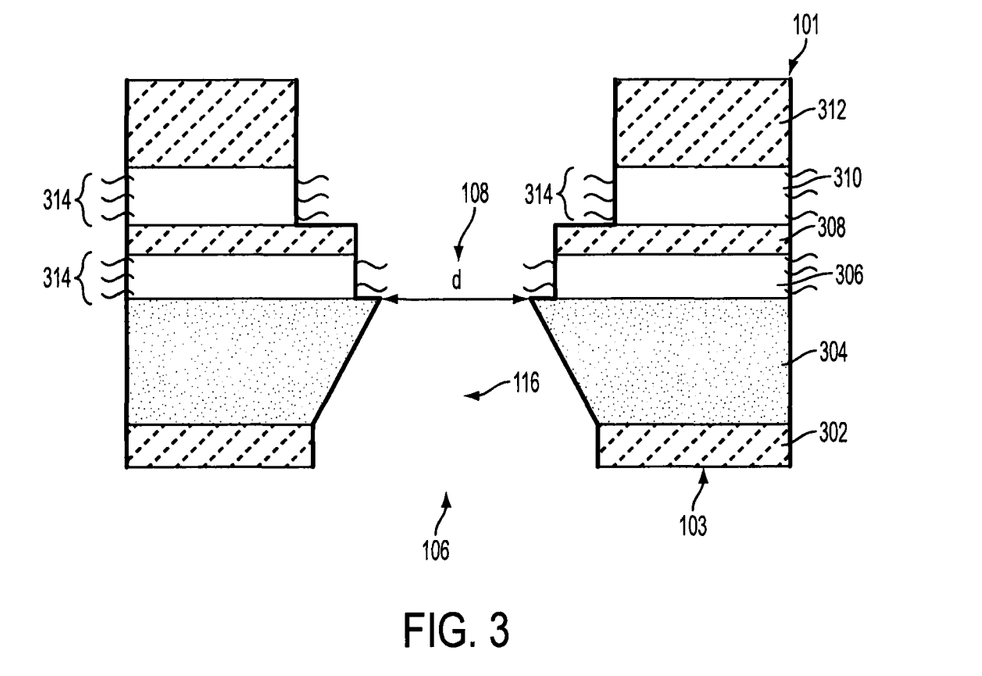
FIG. 3 illustrates a detailed view of the nanopore chip of the nanopore device of FIG. 1.

FIG. 3 illustrates the nanopore chip 106, which is sealingly disposed between the first and second cell portions 102, 104, respectively (see FIG. 1). The thicknesses and composition of the nanopore chip 106 can vary and can be tailored for the intended application. Thus, the compositions and thicknesses described are not intended to be limited. In one embodiment, the nanopore chip 106 has a multi-layer structure including silicon dioxide. In another embodiment, the multi-layer structure of the nanopore chip 106 includes more than one layer of silicon dioxide. The silicon dioxide layer has a thickness of about 20 nm to 35 nm; in another embodiment, the thickness varies from about 25 nm to 70 nm. In yet other embodiments, the thickness is from about 20 nm to 200 nm.

In an exemplary embodiment, the nanopore chip 106 includes a layer 302 of, for example, silicon nitride having a thickness of approximately 100 nm to 2000 nm that defines the second surface 103. In other embodiments the layer 302 can vary in thickness from about 500 nm to 700 nm. Yet, in other embodiments, the thickness of layer 302 can be about 300 nm to 500 nm. A layer 304 of, for example, silicon having a thickness of approximately 500 nm to 2000 micrometers (µm) is disposed on the layer 302. In other embodiments, layer 304 can vary in thickness in the range of about 250 nm to 1000 µm. In yet other embodiments, the thickness can vary in the range of about 500 µm to 550 µm. A layer 306 of silicon dioxide, which is described above, is disposed on the layer 304 which can vary in thickness between about 20 nm to 35 nm. In other embodiments, thickness of layer 306 can vary from about 25 nm to 70 nm, and in yet other embodiments, the thickness can vary from about 20 nm to 200 nm. A layer 308 of, for example, silicon nitride having a thickness of, for example, approximately 30 nm to 50 nm, is disposed on the layer 306. In other embodiments, thickness of layer 308 can vary from about 30 nm to 100 nm, and in yet other embodiments, thickness of layer 308 can vary from about 30 nm to 200 nm. A layer 310 of, for example, silicon dioxide, is disposed on layer 308. Layer 310 has a thickness of, for example, approximately 20 nm to 35 nm. In other embodiments, it can vary from about 25 nm to 70 nm, and in yet others it can vary from about 20 nm to 200 nm. A layer 312 of, for example, silicon nitride having a thickness of approximately 500 nm to 700 nm that defines the first surface 101 is disposed on the layer 310. In other embodiments the silicon nitride thickness can vary from about 300 nm to 800 nm, and in yet others it can be about 100 nm to 2000 nm. Surfaces of the silicon dioxide, including the aperture 108, are functionalized with a monosilane 314, which is described in greater detail below.

The multi-layer structure of the nanopore chip 106 may be fabricated using any suitable fabrication process that may include, for example, chemical vapor deposition (CVD), plasma enhanced chemical vapor deposition (PECVD), lithographic patterning and etching, and epitaxial growth processes. Subsequently, the nanopore 108 can be fabricated through the multi-layer structure of the nanopore chip 106 by any suitable process that can include electron beam drilling or ion beam drilling. The nanopore chip 106 is but an exemplary embodiment. Other embodiments of the nanopore chip 106 may be used.

As mentioned above, at least the surface of the multi-layer structure defining the aperture 108 and comprising the minimal diameter comprise a monosilane 314 functionalized silicon dioxide having a silicon-oxygen-silicon bond. The monosilane functionalized silicon dioxide is formed by reaction of a monosilane with silanol groups present on the silicon dioxide surface, which is also known as silylation. Silylation involves covering of a surface, for example silicon dioxide, through self-assembly with organofunctional alkoxysilane molecules. A general reaction scheme is shown as follows:

SILANOL
GROUPS

MONOSILANE

FUNCTIONALIZED
SILICON DIOXIDE wherein n is an integer from 1 to 12, $R_1$ is a methyl group, an ethyl group, a propyl group, a butyl group, a pentyl group, or a hexyl group; $R_2$ and $R_3$ are each independently a methyl group, an ethyl group, a propyl group, an isopropyl group, a butyl group, or a tert-butyl group; and $R_4$ is a chloride, a carboxylic acid group, an amino group, an amide group, a thiol group, an alcohol group, an acyl chloride group, an acyl bromide group, an acyl iodide group, an alkene group, an alkyne group, or a polyether group.

The monosilane substantially forms a monolayer on a surface of the silicon dioxide. The monolayer has a thickness of about 0.5 nm to about 4 nm. In one embodiment, the monolayer has a thickness of about 1 nm to about 2 nm. In another embodiment, the monolayer has a thickness of about 2 nm to about 4 nm. In one embodiment, the monosilane functionalized silicon dioxide has the following structure:

wherein n is an integer from 1 to 12; $R_2$ and $R_3$ are each independently a methyl group, an ethyl group, a propyl group, an isopropyl group, a butyl group, or a tert-butyl group; and $R_4$ is a chloride, a carboxylic acid group, an amine group, an amide group, a thiol group, an alcohol group, an acyl chloride group, an acyl bromide group, an acyl iodide group, an alkene group, an alkyne group, or a polyether group. In one embodiment, the monosilane functionalized silicon dioxide is formed by reaction of is 3-aminopropyl-dimethyl-ethoxysilane with silanol groups present on the silicon dioxide surface.

Figure 4:
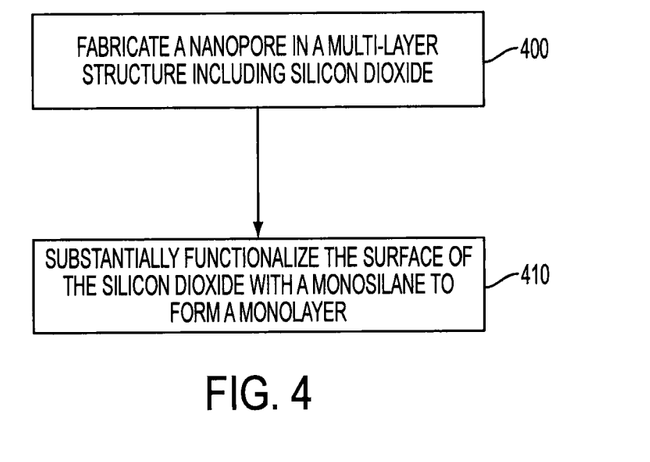
FIG. 4 illustrates a block diagram of an exemplary method for making the nanopore device of FIG. 1.

FIG. 4 illustrates a block diagram of an exemplary method for making a nanopore device 100, in particular functionalizing a silicon dioxide surface of a nanopore chip 106 with monosilane 314. In block 400, a nanopore 108 is fabricated in a multi-layer structure including silicon dioxide (e.g., layers 306 and 310 in FIG. 3), for example, by electron beam drilling or ion beam drilling, to form the nanopore chip 106. In block 410, an exposed surface of the silicon dioxide is substantially functionalized with a monosilane to form a silicon-oxygen-silicon bond and a monolayer on the surface of the silicon dioxide. The monosilane functionalized silicon dioxide has the following structure:

wherein n is an integer from 1 to 12; $R_2$ and $R_3$ are each independently a methyl group, an ethyl group, a propyl group, an isopropyl group, a butyl group, or a tert-butyl group; and $R_4$ is a chloride, a carboxylic acid group, an amine group, an amide group, a thiol group, an alcohol group, an acyl chloride group, an acyl bromide group, an acyl iodide group, an alkene group, an alkyne group, or a polyether group.

An exemplary method for substantially functionalizing the silicon dioxide surface of the nanochip 106 includes adding the monosilane 314 to a solution or solvent to form a monosilane solution, and then adding the solution to the nanopore chip 106. Non-limiting examples of suitable solutions and solvents include aqueous solutions and organic solvents, for example, toluene, ethanol, hexane and dichloromethane. The monosilane 314 solution can be added to the multi-layer structure at a first temperature, and then the first temperature can be increased to a second temperature for a period of time. Optionally, the first temperature is room temperature. In one embodiment, the second temperature is room temperature. In another embodiment, the second temperature is about 50° C. to about 110° C.; about 99° C. to about 200° C.; or about 90° C. to about 110° C.

The second temperature can be maintained for a period of time sufficient to allow functionalization of the silicon dioxide surface. For example, the monosilane solution can be added to the nanopore chip 106 and allowed to react for about 16 hours to about 36 hours. Alternatively, the monosilane solution is added to the nanopore chip 106 and allowed to react with the silicon dioxide for about 1 hour to about 24 hours. In one embodiment, the monosilane solution is allowed to react with the silicon dioxide of the nanopore chip 106 for about 24 hours to about 72 hours. The exemplary method in FIG. 4 is not intended to be limiting. As such, other suitable methods of fabricating the nanopore 108, the nanopore chip 106, or functionalizing a surface of the silicon dioxide can be used.

Optionally, the aperture 108 surface or entire nanopore chip 106 can be cleaned before or after functionalization of the silicon dioxide portion of the nanopore chip 106. A non-limiting example of a cleaning method includes soaking the nanopore chip 106 in acidic solution for a period of time. Non-limiting examples of acidic solutions include, but are not limited to, nitric acid solutions, nitric acid/hydrogen peroxide mixtures, sulfuric acid solutions, sulfuric acid/hydrogen peroxide mixtures, hydrochloric acid solutions, and hydrochloric acid/hydrogen peroxide mixtures. Alternatively, the nanopore chip 106 can be soaked in any desired cleaning solution, for example, piranha solution, chromic acid solution, or a high pH surfactant solution (pH≥11). Optionally, the temperature is increased during the cleaning step to a temperature of about 50° C. to about 120° C. or maintained at room temperature. Alternatively, the temperature is increased to about 70° C. to about 100° C. The nanopore chip 106 can be soaked in the cleaning solution for a period of time, for example, about 1 minute to about 3 hours. Alternatively, the nanopore chip 106 is soaked for a period of time of about 2 hours to about 6 hours. Following functionalization of the silicon dioxide with the monosilane 314, optionally, the nanopore chip 106 can be rinsed, dried, and stored.

When the silicon dioxide surface of the nanopore chip 106 is substantially functionalized with the monosilane 314, (e.g., as shown in FIG. 3, on surfaces of silicon dioxide layers 306 and 310) some properties or surface characteristics of the aperture 108 can be altered. The surface characteristic altered depends on the degree of functionalization, dimensions of the nanopore, conditions, and particular monosilane used. Non-limiting examples of altered surface characteristics include surface charge, polarity, pH sensitivity, and hydrophobicity. In addition, as exemplified below, the substantially functionalized silicon dioxide surface of the nanopore chip 106 provides a substantially stable ionic current and substantially linear ionic current between −1 Volt (V) and +1 Volt (V), compared to an non-functionalized silicon dioxide nanopore.

A method for operating a nanopore device 100, referring to FIG. 2, includes filling a first cavity 112 and a second cavity 116 of the nanopore device 100 with a first buffered salt solution, introducing an analyte into the first cavity 100, applying a voltage in the nanopore device, and measuring a current in the nanopore device. The current has a current path defined by the first cavity 112, the second cavity 116, and the aperture 108 communicative with the first cavity 112 and the second cavity 116, and the current is affected by the analyte passing proximate to or through the aperture.

The buffered salt solution is introduced into the first cavity 112 via the first port 118 and the second cavity 116 via the third port 122. The buffered salt solution may be flushed from the first cavity 112 via the second port 120, and the second cavity 116 via the fourth port 124. However, in alternate embodiments, the roles of the ports may be reversed. The electrodes 201 and 203 are communicative with the buffered salt solution. The ionic current in the current path is measured by the current sensing device 204 that may be connected to a processing and display device 206 that may include, for example, a computer processor and display operative to process the sensed current values and output a logical result to a user on the display. As mentioned above, the current is affected by analytes passing through the nanopore 108. Thus, the analyte may be introduced into the first cavity 112 via the first port 118. Non-limiting examples of analaytes include deoxyribonucleic acid (DNA), ribonucleic acid (RNA), proteins, and combinations thereof. The molecules affect the measured current as the molecules pass proximate to or through the nanopore 108.

Prior to using the nanopore device 100 to measure the presence of molecules in the fluid, the nanopore device 100 is prepared using an exemplary "wetting" method described below. The wetting method physically prepares the nanopore device 100 for operation, and includes a testing method that is used to determine whether the nanopore device 100 meets desired current specifications and is calibrated to desired thresholds. When the nanopore device 100 produces an unstable ionic current, the device may not be used for analysis. Instead, a substantially stable and linear ionic current may be desired. The monosilane functionalized silicon dioxide of the nanopore chip 106 can provide a substantially stable and linear ionic current.

Figure 5:
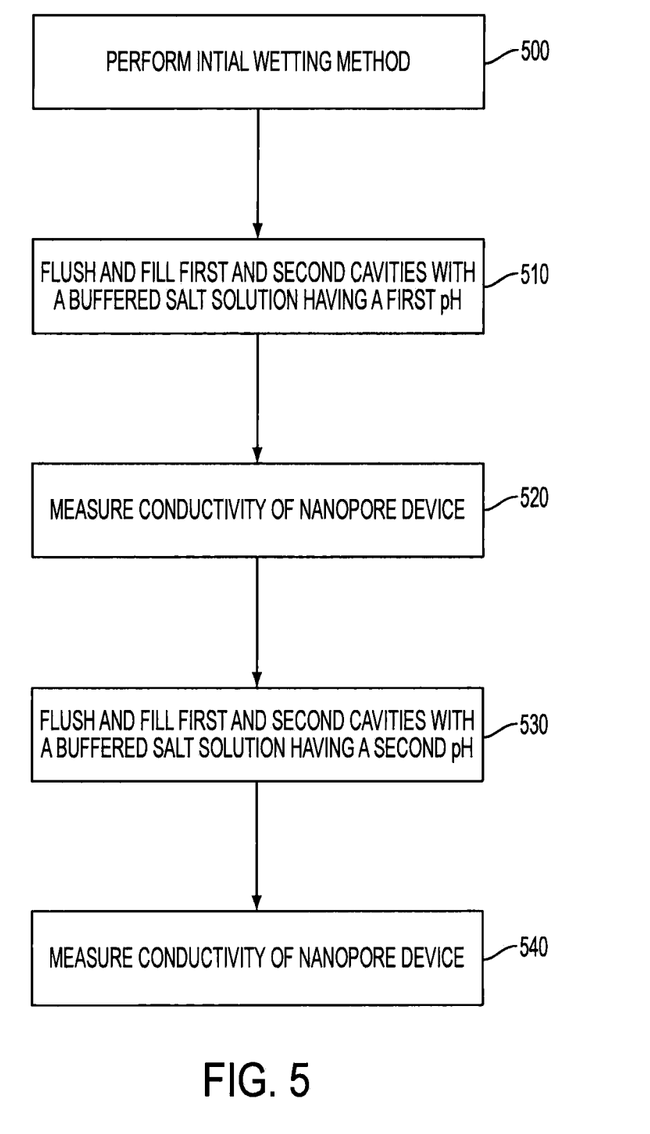
FIG. 5 illustrates a block diagram of an exemplary method for wetting the nanopore device of FIG. 1.

In this regard, FIG. 5 illustrates a block diagram of an exemplary method for wetting the nanopore device 100. In block 500, an initial wetting method is performed. The initial wetting method may include for example, flushing and filling one of the cavities 112 or 116 with a volatile solvent with much lower surface tension than water, for example ethanol or isopropyl alcohol (IPA), and ensuring that there is no air gap or air bubble in the fluidic pathway. Waiting for a time period (e.g., from about 1 minute, or at least about 5 minutes) allows vapor diffusion through the aperture 108 (of FIG. 1). Once the time period has expired, the remaining empty cavity 112 or 116 is flushed and filled with the volatile solvent. Another waiting period (e.g., at least five minutes) may be observed to complete the initial wetting method. Following the initial wetting method, the volatile solvent is flushed from the cavities 112 and 116 and replaced with a buffered salt solution. For example, in block 510, the first cavity 112 and the second cavity 114 are flushed and filled with a buffered salt solution having a first pH. In block 520, the conductivity of the nanopore device 100 is tested by applying a voltage and measuring the ionic current in the fluid flow path for a time period (e.g., at least about 30 minutes) to determine whether the current increases and stabilizes during the time period. The desired ionic current depends on the device application. Optionally, to optimize or increase the ionic current of the nanopore device 100, the first and second cavities 112 and 114 can be flushed and filled with a buffer solution having a second pH (block 530). In block 540, the conductivity of the nanopore device is re-tested. The first pH and the second pH of the buffered salt solutions can be within any pH range, which depends on the application. For example, the first or second pH of the buffered salt solution can be about 5 to about 10. Alternatively, the first or second pH of the buffered salt solution can be about 0 to about 13, or about 6 to about 11. In an exemplary embodiment, the buffered salt solution can be a 1 molar (M) potassium chloride buffer solution with a pH of about 8 to about 9.8.

Optionally, if the measured current has not increased following the introduction of the buffered salt solution in block 510, the first and second cavities 112 and 116 may each be flushed and kept filled with a buffered salt solution having a pH of approximately 3 to about 6 (not shown). Following a period of hours or days, the device conductivity re-measured (not shown).

Other initial wetting methods may include, for example, a plasma cleaning method, a piranha cleaning method that uses a concentrated sulphuric acid and hydrogen peroxide solution, or an electro wetting method that applies large direct current voltage pulses to the nanopore device 100.

The exemplary methods of operation and wetting described above are not limited to the exemplary solutions described. For example, any salt concentration may be used, and any pH values of the buffer solutions may be used. The pH values and the salt concentrations of the buffered salt solutions used in the embodiments described above are chosen in part to accommodate a particular type of analyte or molecule that will be measured by the nanopore device 100. If another type of analyte will be measured by the nanopore device 100, alternate buffer salt solutions having, for example, different pH and salt concentrations may be used. Non-limiting examples of salts include alkali halide solutions, such as $CaCl_2$, $MgCl_2$, LiCl, NaCl, CsCl and RbCl.

The method and degree of monosilane functionalization of the silicon dioxide portion of the nanopore chip 106 can be modified and tailored to achieve the desired ionic current. For some applications, such as DNA translocation studies, it is desired that the ionic current be stable and/or greater than a desired threshold value following an applied voltage. In addition, it may be desired that the ionic current be substantially linear, following an applied voltage, as illustrated in the Example 2 below. Following a determination that the measured current in the nanopore device 100 meets design specifications, the translocations of an analyte introduced into a buffered salt solution in the first cavity 112 may be measured.

EXAMPLES

Comparative Example 1

Figure 6A:
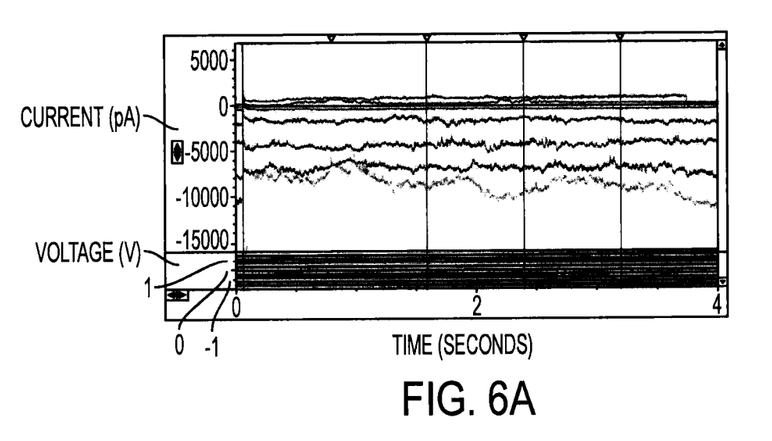
FIG. 6A illustrates comparative test results of measured nanopore current over time within a nanopore device without a monosilane functionalized silicon dioxide nanopore.
Figure 6B:
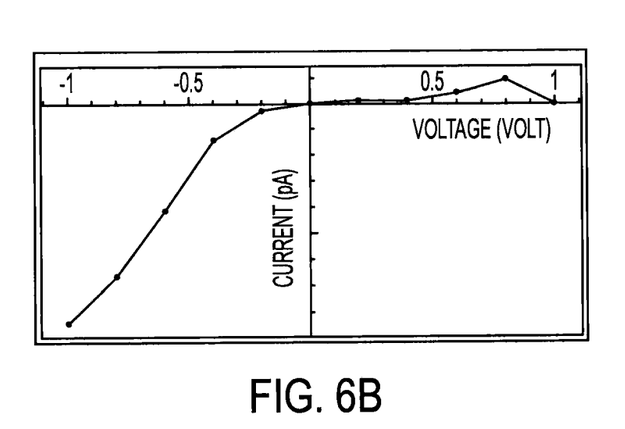
FIG. 6B illustrates comparative test results of measured nanopore current as a function of applied voltage within a nanopore device without a monosilane functionalized silicon dioxide nanopore.

FIGS. 6A and 6B illustrate comparative test results of measured ionic currents in a nanopore device 100 with a non-functionalized nanopore chip 106. The nanopore had a diameter of about 15 nm. First cavity 112 and second cavity 114 were flushed and filled with a 1 M potassium chloride buffer solution (pH 8), a voltage was applied, and the ionic current was measured. The traces in FIG. 6A show measured ionic currents, as functions of different applied voltages, over time. As demonstrated, the measured ionic current is both unstable and smaller than the expected current at 1 V (~85 nA) according to Ohm's law (Pore_Resistance=Voltage/Pore_current=(Resistivity_of_salt solution)*(pore_membrane_thickness/pore_area). Further, FIG. 6B demonstrates that the measured ionic current as a function of applied voltages is not substantially linear from −1 V to +1 V. These current properties, i.e., being substantially unstable and non-linear, are not suitable for DNA translocation studies.

Example 2

Figure 7A:
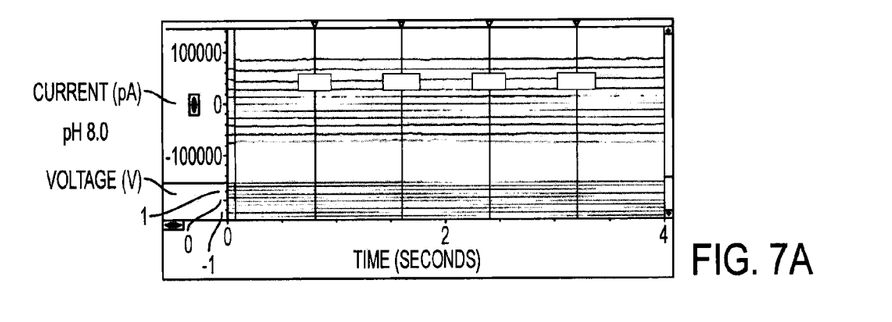
FIGS. 7A and 7B illustrate test results of measured nanopore current over time within a nanopore device with a monosilane functionalized silicon dioxide nanopore.
Figure 7B:
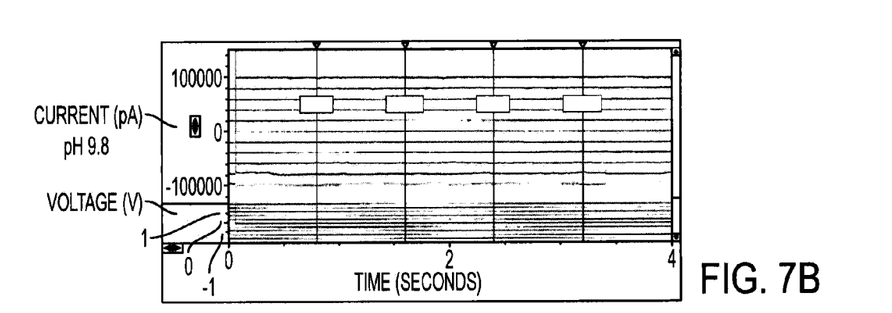
Figure 7C:
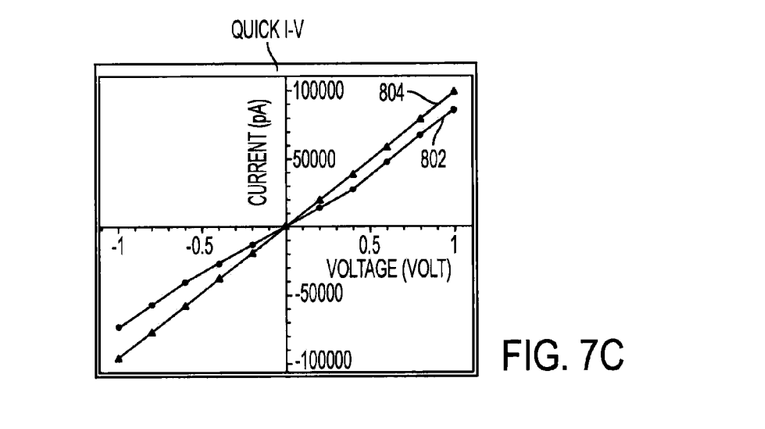
FIG. 7C illustrates test results of measured nanopore current as a function of applied voltage within a nanopore device with a monosilane functionalized silicon dioxide nanopore.

FIGS. 7A-C illustrate test results of measured ionic currents in a nanopore device 100 with a nanopore chip 106 having monosilane functionalized silicon dioxide. The nanopore diameter was 14 nm. The nanopore device 100 and functionalization was performed as described in the above embodiments. Specifically, the nanopore chip 106 was incubated in a toluene solution of APDMES for 24 hours at 99° C. First cavity 112 and second cavity 114 were flushed and filled with a 1 M potassium chloride buffer solution with a pH of 8.0 (FIGS. 7A and C). A voltage was applied, and the ionic current was measured. Then, first cavity 112 and second cavity 114 were flushed and filled with a 1 M potassium chloride buffer solution with a pH of 9.8 (FIGS. 7B and 7C).

FIGS. 7A-B graphically illustrate measured ionic current and voltage as a function of time at a pH of 8.0 and 9.8, respectively. FIG. 8C illustrates measured ionic current as a function of applied voltages. Compared to the non-functionalized nanopore chip of FIG. 6A-B, functionalizing the exposed surfaces of the silicon dioxide in the nanopore chip 106 with monosilane 314 provides the nanopore device 100 with a substantially stable ionic current at both pH 8.0 (FIG. 7A) and pH 9.8 (FIG. 7B). In addition, lines 802 (pH 9.8) and 804 (pH 8.0) illustrate that the measured current is substantially linear between −1 V and +1 V. Further, at 1), the measured current increased from 85 nA without the monosilane to 100 nA, which was expected for an Ohmic conductor.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

What is claimed is:

1. A nanopore device comprising:
a multi-layer structure comprising at least one layer of silicon dioxide extending from an outer edge of the multi-layer structure to a surface defining an aperture extending through the multi-layer structure, wherein at least the surface comprising a minimal diameter consists essentially of a monosilane functionalized silicon dioxide having a silicon-oxygen-silicon bond, the monosilane functionalized silicon dioxide having the following structure:

wherein n is an integer from 1 to 12; $R_2$ and $R_3$ are each independently a methyl group, an ethyl group, a propyl group, an isopropyl group, a butyl group, or a tert-butyl group; and $R_4$ is a chloride, a carboxylic acid group, an amine group, an amide group, a thiol group, an alcohol group, an acyl chloride group, an acyl bromide group, an acyl iodide group, an alkene group, an alkyne group, or a polyether group.

2. The nanopore device of claim 1, wherein the monosilane functionalized silicon dioxide is formed by reaction of a monosilane with silanol groups present on a surface of the silicon dioxide.

3. The nanopore device of claim 2, wherein the monosilane functionalized silicon dioxide is formed by reaction of 3-aminopropyl-dimethyl-ethoxysilane with silanol groups present on the surface of the silicon dioxide.

4. The nanopore device of claim 1, wherein the multi-layer structure comprising the surface defining the aperture comprises at least one layer of silicon dioxide at a thickness of about 20 nm to about 200 nm.

5. The nanopore device of claim 1, wherein the minimal diameter of the aperture is about 5 nm to about 60 nm.

6. The nanopore device of claim 1, wherein a surface characteristic of the aperture is modified.

7. The nanopore device of claim 6, wherein the surface characteristic is surface charge, polarity, pH sensitivity, or hydrophobicity.

8. The nanopore device of claim 1, wherein the multi-layer structure comprising the surface defining the aperture further comprises at least one layer of a silicon nitride layer.

9. The nanopore device of claim 1, wherein the aperture further comprises first and second cavities being fluidically connected via the aperture.

10. The nanopore device of claim 9, further comprising a voltage source and a current sensing device operative to detect changes in a current within the nanopore device, the current having a current path defined by the first cavity, the second cavity, and the aperture.

11. The nanopore device of claim 10, wherein the current is substantially stable and substantially linear between −1 Volt (V) and +1 V.

12. A method for making a nanopore device, the method comprising:
fabricating an aperture in a multi-layer structure comprising at least one layer of silicon dioxide extending from an outer edge of the multi-layer structure to a surface defining an aperture extending through the multi-layer structure; and
substantially functionalizing an exposed surface of the at least one layer of silicon dioxide with a monosilane to form a silicon-oxygen-silicon bond and a monolayer on the surface of the silicon dioxide;
wherein at least the surface comprising a minimal diameter consists essentially of the monosilane functionalized silicon dioxide having the following structure:

wherein n is an integer from 1 to 12; $R_2$ and $R_3$ are each independently a methyl group, an ethyl group, a propyl group, an isopropyl group, a butyl group, or a tert-butyl group; and $R_4$ is a chloride, a carboxylic acid group, an amine group, an amide group, a thiol group, an alcohol group, an acyl chloride group, an acyl bromide group, an acyl iodide group, an alkene group, an alkyne group, or a polyether group.

13. The method of claim 12, further comprising cleaning a surface of the aperture prior to substantially functionalizing the surface of the silicon dioxide.

14. The method of claim 12, wherein the minimal diameter of the aperture is about 5 nm to about 60 nm.

15. The method of claim 12, wherein the monosilane functionalized silicon dioxide is formed by reaction of 3-aminopropyl-dimethyl-ethoxysilane with silanol groups present on the surface of the silicon dioxide.

16. The method of claim 12, wherein substantially functionalizing the surface of the aperture comprises adding the monosilane in a solution to the multi-layer structure at a first temperature and then increasing the first temperature to a second temperature for a period of time.

17. The method of claim 16, wherein the second temperature is about 90 degrees Celsius to about 130 degrees Celsius.

18. A nanopore device comprising:
a multi-layer structure comprising at least one layer of silicon dioxide extending from an outer edge of the multi-layer structure to a surface defining an aperture extending through the multi-layer structure, wherein at least the surface comprising a minimal diameter consists essentially of a monosilane functionalized silicon dioxide having a silicon-oxygen-silicon bond, the monosilane functionalized silicon dioxide having the following structure:

wherein n is an integer from 1 to 12; $R_2$ and $R_3$ are each independently a methyl group, an ethyl group, a propyl group, an isopropyl group, a butyl group, or a tert-butyl group; and $R_4$ is an amino group; and the monosilane functionalized silicon dioxide comprises a monosilane monolayer having a thickness of about 0.5 to about 4 nanometers.

19. The nanopore device of claim 18, wherein the monosilane functionalized silicon dioxide is formed by reaction of is 3-aminopropyl-dimethyl-ethoxysilane with silanol groups present on the silicon dioxide surface.

* * * * *